(12) United States Patent
Crump et al.

(10) Patent No.: US 6,584,970 B1
(45) Date of Patent: Jul. 1, 2003

(54) RETAINING PLUG FOR ENDOTRACHEAL CATHETER AND MANIFOLD ASSEMBLY AND METHOD OF USE

(75) Inventors: Chet M. Crump, Draper, UT (US); Edward B. Madsen, Riverton, UT (US)

(73) Assignee: Ballard Medical Products, Draper, UT (US)

( * ) Notice: Subject to any disclaimer, the term of this patent is extended or adjusted under 35 U.S.C. 154(b) by 0 days.

(21) Appl. No.: 09/413,209

(22) Filed: Oct. 5, 1999

(51) Int. Cl.[7] ............................................. A61M 15/00
(52) U.S. Cl. ........................ 128/200.24; 128/202.27; 128/207.16
(58) Field of Search ................... 251/89.5, 284, 251/357; 4/286; 215/355; 220/322, 323, 801; 128/200.24, 202.27, 200.26, 207.16, 912

(56) References Cited

U.S. PATENT DOCUMENTS

| | | | |
|---|---|---|---|
| 378,744 A | * | 2/1888 | Underwood |
| 391,870 A | * | 10/1888 | Walter |
| 474,436 A | * | 5/1892 | Barnhart |
| 535,390 A | * | 3/1895 | Murphy |
| 587,350 A | * | 8/1897 | Wear |
| 675,622 A | * | 6/1901 | Clinton |
| 837,812 A | * | 12/1906 | Eimer |
| 924,848 A | * | 6/1909 | Smith |
| 1,052,363 A | * | 2/1913 | Moore |
| 1,162,443 A | * | 11/1915 | Bogdanffy |
| 1,218,662 A | * | 3/1917 | Ingram |
| 1,377,568 A | * | 5/1921 | Ellis et al. |
| 1,730,202 A | * | 10/1929 | Geyer |
| 1,800,045 A | * | 4/1931 | Bates |
| 2,077,516 A | * | 4/1937 | Dart |
| 2,409,753 A | * | 10/1946 | Harrison et al. |
| 2,444,889 A | * | 7/1948 | Braidwood |
| 2,771,308 A | * | 11/1956 | Vitcha et al. ............... 251/89.5 |
| 3,084,713 A | * | 4/1963 | Parrish ........................ 251/89.5 |
| 3,086,747 A | * | 4/1963 | Saner .......................... 251/89.5 |
| 3,129,919 A | * | 4/1964 | Evans ......................... 251/89.5 |
| 3,148,798 A | * | 9/1964 | Brown |
| 3,858,910 A | * | 1/1975 | Oetiker ....................... 251/89.5 |
| 3,991,762 A | | 11/1976 | Radford |
| 4,248,236 A | | 2/1981 | Linder |
| 4,409,692 A | * | 10/1983 | Ness .............................. 4/286 |
| 4,510,933 A | | 4/1985 | Wendt et al. |
| 4,569,344 A | | 2/1986 | Palmer |
| 4,809,871 A | * | 3/1989 | Angelchik ................... 220/307 |
| 5,325,850 A | | 7/1994 | Ulrich et al. |
| 5,330,152 A | * | 7/1994 | Visco ......................... 251/89.5 |
| 5,382,242 A | * | 1/1995 | Horton et al. ............... 604/283 |
| 5,482,171 A | * | 1/1996 | Palmer ........................ 215/228 |
| 5,513,628 A | | 5/1996 | Coles et al. |
| 5,562,618 A | | 10/1996 | Cai et al. |
| 5,582,165 A | * | 12/1996 | Bryan et al. ........... 128/207.14 |
| 5,791,337 A | | 8/1998 | Coles et al. |

FOREIGN PATENT DOCUMENTS

| | | |
|---|---|---|
| FR | 1449918 | 11/1966 |
| FR | 2528707 | 12/1983 |
| WO | WO 9526772 | 10/1995 |
| WO | WO 9626757 | 9/1996 |
| WO | WO 9805371 | 2/1998 |

OTHER PUBLICATIONS

PCT International Search Report Jan. 16, 2001.

* cited by examiner

*Primary Examiner*—Aaron J. Lewis
(74) *Attorney, Agent, or Firm*—Dority & Manning, P.A.

(57) ABSTRACT

The present invention provides a plug for a respiratory suction catheter and manifold assembly that protects or maintains at least one internal component, such as the flap, of an assembly during nonuse. In a preferred embodiment, the interior plug element functions or contains a spring or similar expanding mechanism. This provides for additional security for the internal components. Further, the plug may contain an exterior plug element as well as an interior plug element.

26 Claims, 16 Drawing Sheets

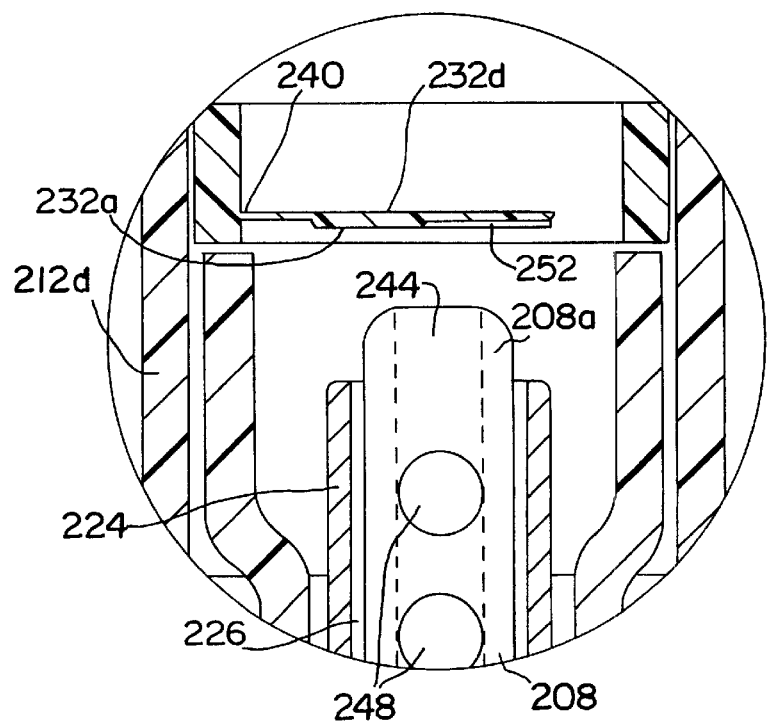
FIG. IC
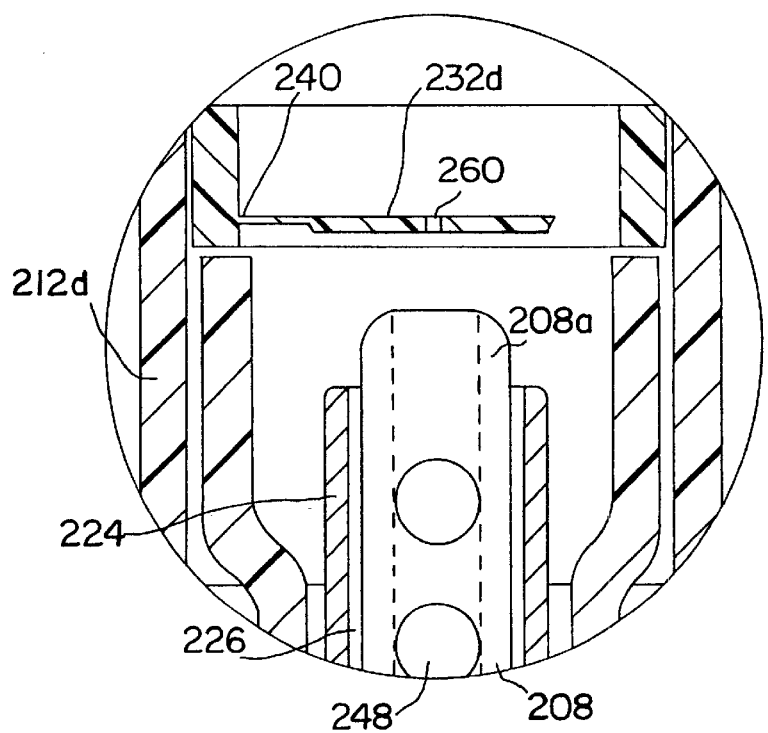
FIG. ID

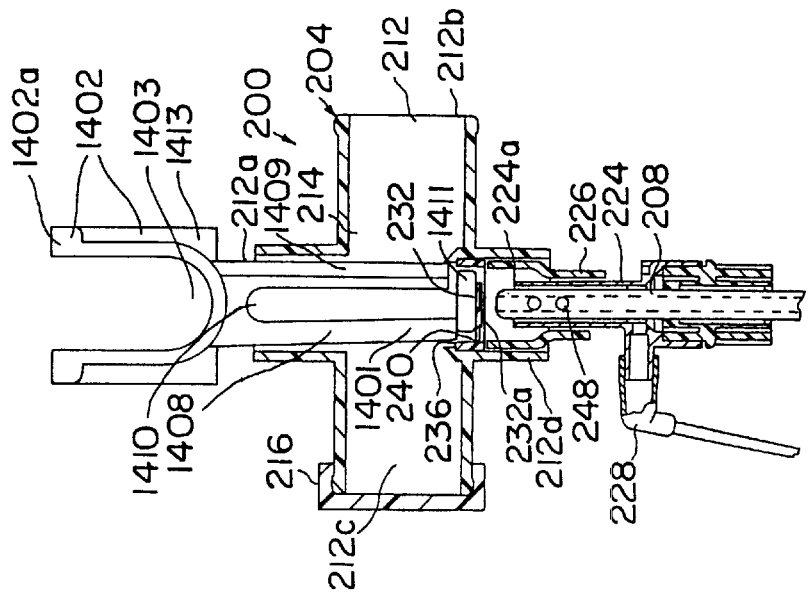
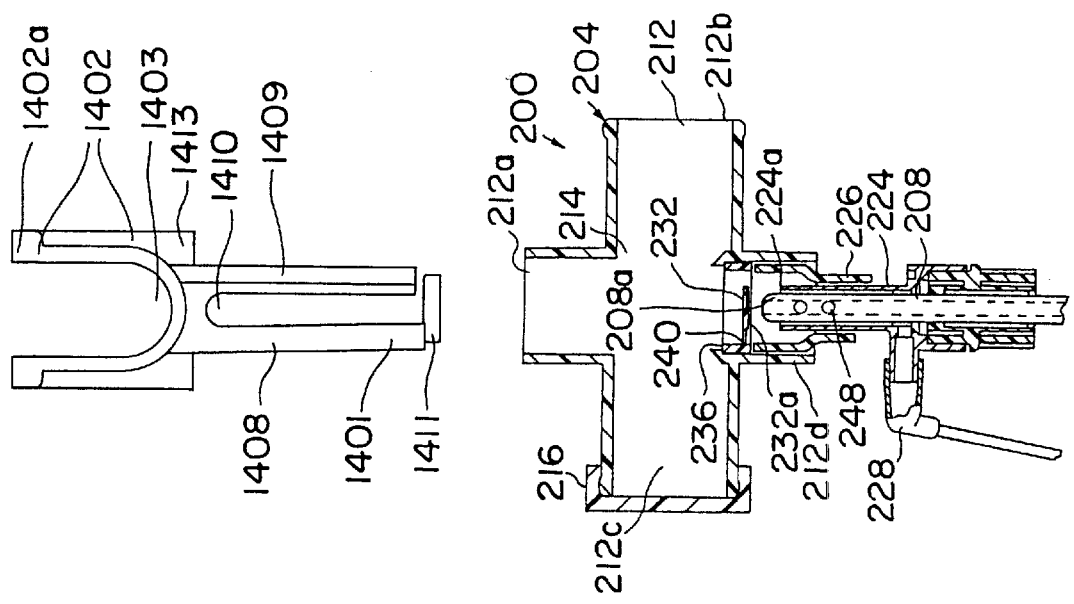

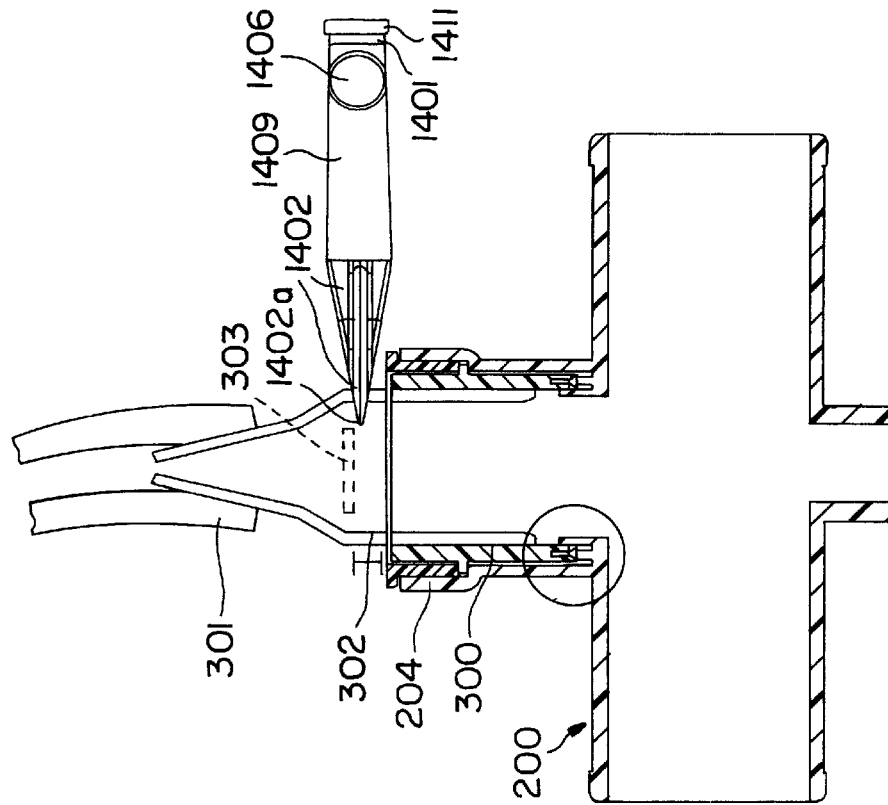
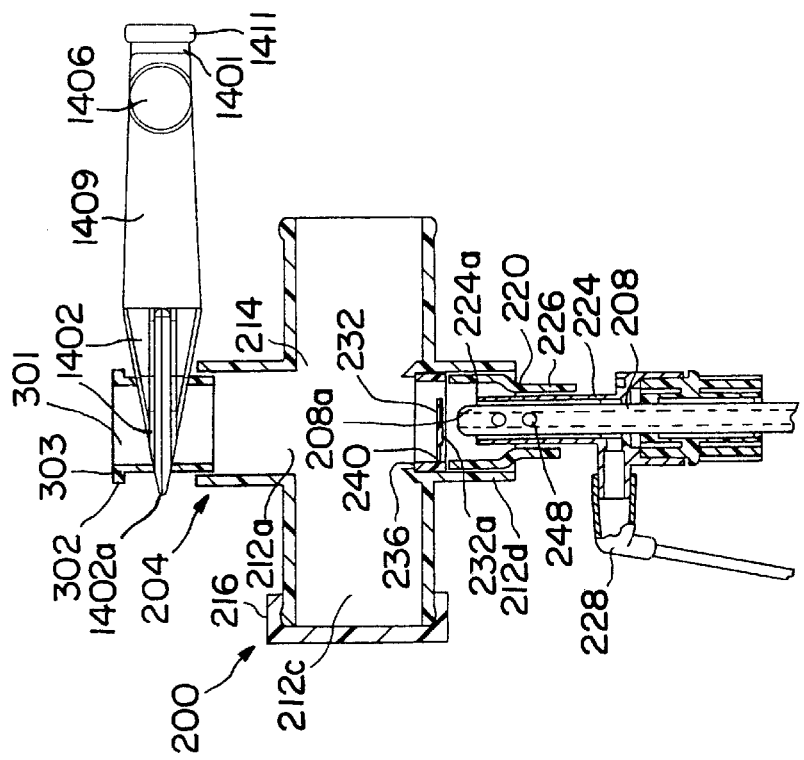
FIG. 8D
FIG. 8C

RETAINING PLUG FOR ENDOTRACHEAL CATHETER AND MANIFOLD ASSEMBLY AND METHOD OF USE

FIELD OF THE INVENTION

The present invention is directed to a retaining plug for use in the protection of internal components, such as flaps, of endotracheal catheter tube and manifold assemblies during nonuse, including storage and shipping. The plug of the invention assists in protection of the inner chamber of the assembly from possible contaminants. In addition, the plug of the invention serves to maintain the flap in a closed position during periods of non-use. By use of the plug, the assembly is in excellent working condition once it reaches its destination In a preferred embodiment, the plug contains an exterior element characterized by at least one wedge-like surface. The exterior element of the plug is usefull for separating the endotracheal catheter tube and other adapters and attachment structures from the manifold without an increased risk of contamination or discomfort to the patient. The invention Other relates to a method of using the retaining plug.

BACKGROUND OF THE INVENTION

In the past twenty years, the medical industry has seen an increased interest in closed suction catheter assemblies to create artificial airways, Such assemblies contain endotracheal catheters and manifolds. For instance, such systems were disclosed in U.S. Pat. No. 3,991,762 ("Radford"), which provided for a catheter within a protective sleeve wherein the catheter may be advanced when suctioning is desired. Further, U.S. Pat. No. 4;569,344 ("Palmer"), offered an improved system to reduce the risk of cross-contamination between the patient and the medical personnel using the device. More recently, interest has developed in catheter systems having a flap by which the internal passageway of the catheter can be closed off from the manifold.

There are a variety of different circumstances for which a person may be required to have an artificial airway, such as an endotracheal catheter tube, placed in the patient's respiratory system. In some circumstances, such as surgery, the artificial airway's function is primarily to keep the patient's airway open so that adequate lung ventilation can be maintained during the procedure. Unfortunately, the internal components of these endotrachcal catheter tube and manifold assemblies may become deformed or otherwise damaged prior to use. For instance, the working requirements of the flap may become nonfunctional if shipped disruptively, thereby causing failure of operation of the flap in actual use. Due to the important function that these endotracheal catheter tube and manifold assemblies serve, it is very important that the internal components be preserved in working condition after shipping, storing, and other periods of nonuse.

Moreover, because the endotracheal tube may be left in the patient for a prolonged period of time, it may become necessary to service these endotracheal catheter tube and manifold assemblies in order to replace, repair, refit, or otherwise manipulate the components of or attached to the assembly. Because patients may need the use of an endotracheal tube to sustain mechanical ventilation for the life of the patient to remove respiratory secretions periodically, it is very useful to be able to manipulate the endotracheal catheter tube and manifold assemblies from a more isolated position while reducing the risk of contamination.

In practice, the respiratory suction catheter is advanced through the inner passageway of the catheter and manifold assembly. As the suction catheter is withdrawn, a negative pressure is applied to the interior of the assembly to draw mucus and other secretions from the patient's respiratory system. While a substantial amount of the mucus and other secretions may be withdrawn through the catheter lumen, a portion of the mucus and other secretions may remain on the outside of the catheter. Because patient secretions can contain infectious agents, such as streptococcus, pseudomonas, staphylococcus, and even HIV, it is important to shield clinicians from contact with the catheter. Likewise, it is important to shield patients from communicable pathogens in the environment and those that may be carried by the clinician. This is particularly important because patients on mechanical ventilation often have compromised immune systems. There exists a need to increase the distance between the clinician and the endotracheal catheter assembly to reduce this risk of contamination.

In addition to concerns of cross-contamination, suctioning a patient's artificial airway potentially interferes with proper respiration. Commonly, indwelling endotracheal tubes used over prolonged periods must be mechanically ventilated. Such patients will typically have a fining or manifold attached to the distal end of the endotracheal tube at an endotracheal tube hub. A pair of ventilator tubes extends from a mechanical ventilator and is typically attached to the manifold by an adapter. One tube provides inspiratory air to the patient for inhalation. The other tube allows for exhaled or expiratory air to exit the system. Once the catheter has been used, interest has been created in easy removal of the catheter from the manifold, particularly at the swivel connections. While the prior art has attempted to combine wedge-like surfaces with U-shaped configuration tools, as discussed herein, the prior art required a discrete unit be separately packaged to perform this function. Moreover, these devices do not provide a significant distance between the clinician and the patient. Moreover, damage to internal components such as the flap has continued to be serious concern to the proper functioning of the catheter assemblies. The prior art fails to incorporate features into a single discrete unit that insure secure insertion and static positioning of the flap during shipping.

SUMMARY OF THE INVENTION

The present invention provides a retaining plug to maintain the position of the internal components of endotracheal catheter tube manifold assemblies, including the flap valve of respiratory suction catheter assemblies during nonuse. Additionally, the present invention may be used to separate the manifold and catheter components, including adapters and attachment structures such as endotracheal tubes, during replacement, transition, and cleaning operations. Moreover, by fabricating the present invention to engage the exterior surface of attachments, swivels, and similar adapters to the manifold, preferably in an engaging relationship created by wedge like surfaces formed on snugly fitting U-shaped tines, the present invention provides a method to separate the manifold from these adapters with minimal discomfort to the patient.

The retaining plug of the present invention is configured to be inserted into the inner shaft of the manifold and thus serves to engage and detain the internal components such as the flap, however configured, within the manifold and catheter assembly. This engaging relationship presses the flap in a closed position and prevents deformation in the shape of the flap as well as upward movement of the flap during shipping, storing, and other periods of nonuse. In the preferred embodiment, the plug comprises at least one spring or similar expanding element. In this embodiment, when properly inserted into the catheter assembly, each spring will expand and engage, thereby forming a snug, friction fit with at least one inner cavity of the assembly. This engaging property will insure that the flap is snugly held in a closed position to prevent deformation or premature intrusion of the catheter during shipping, storing, or nonuse. In a preferred embodiment, the spring will expand into at least one cavity of the manifold through its preformed knob on the external wall of the spring. This protruding knob engages into a receptor port of the manifold of this cavity.

BRIEF DESCRIPTION OF THE DRAWINGS

The above and other objects, features and advantages of the invention will become apparent from a consideration of the following detailed description presented in connection with the accompanying drawings in which:

FIG. 1C shows a fragmented, close-up cross-sectional view of the representative respiratory suction catheter apparatus shown in FIG. 1A;

FIG. 1D shows a fragmented, close-up cross-sectional vies of another embodiment of a respiratory suction catheter apparatus shown in FIG. 1A;

FIG. 7C shows an exploded front view showing the interior and exterior plug elements of an alternative embodiment of the present invention being inserted into a cross-sectional view of a representative manifold and catheter assembly;

FIG. 7D shows a front view showing the interior and exterior plug elements of the plug of FIG. 7C inserted into a cross-sectional view of a representative manifold and catheter assembly;

FIG. 8C shows an embodiment of the present invention, of the plug of FIGS. 5A–5D, comprising a U-shaped formation engaging the exterior surface of the cross-sectional view of an attachment or adaptor to a manifold;

FIG. 8D shows a cross-sectional view of an embodiment of the present invention, of the plug of FIGS. 5A–5D, comprising a U-shaped formation the exterior surface of the cross-sectional view of a representative attachment in the form of an endotrachcal tube that is attached via a swivel connection;

DETAILED DESCRIPTION OF PREFERRED EMBODIMENT

As used herein, distal refers generally to the direction of the patient, while proximal refers to the direction of the clinician. As shown in FIGS. 1A–1D, 6A–6B, 7A–7F, 8A–5D, and 9A–9B, the assembly has been oriented such that the distal (patient) end is toward the top of the page while the proximal (clinician) end is toward the bottom of the page.

Figure 1A:
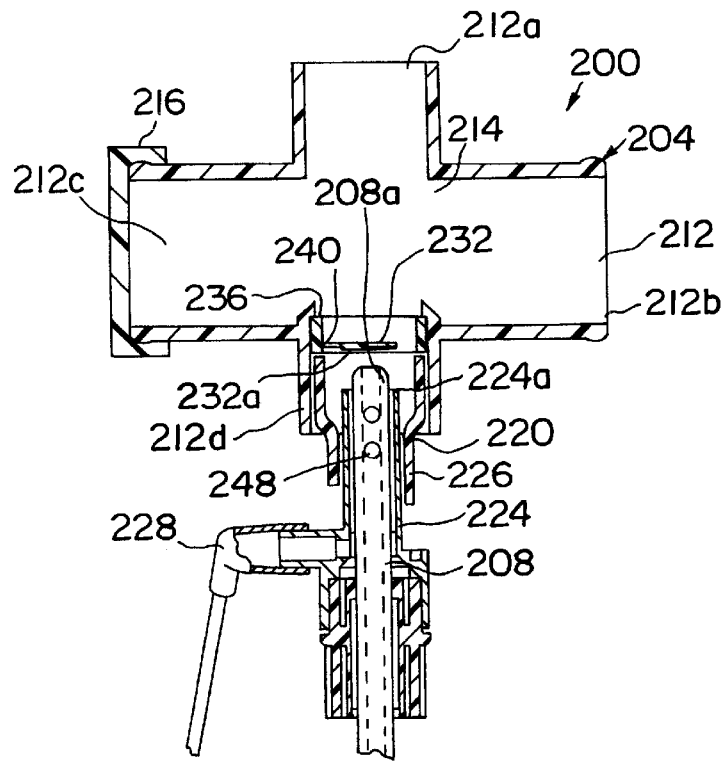
FIG. 1A shows a cross-sectional view of a representative manifold and distal portion of a catheter of a respirator, suction catheter apparatus with a valve member in a closed position.

Various catheter and manifold assemblies are known in the prior art Referring to FIG. 1A, a cross-sectional view of a portion of a representative endotracheal catheter assembly 200, the endotracheal catheter assembly includes a manifold 204 and a catheter 208. The manifold 204 may include a plurality of ports, such as the four ports illustrated by 212a–212d. Alternatively, the manifold may have fewer than four ports. In some situations, a manifold comprising three ports, may be used. The addition of adaptors and attachments may increase the number of paths of ingress and egress of the assembly through the ports. Typically, a first port 212a is configured for attachment to an artificial airway, such as the hub of an endotracheal tube, tracheotomy tube, etc. A second port 212b is typically connected to a pair of ventilator tubes bat means of an adaptor, in accordance with common practice in the in. Additional ports, when included, such as 212c and 212d allow for additional flexibility in configuring the assembly.

During usage, conditioned inspiratory air is forced through one of the ventilator tubes, through the second port 212b and the first port 212a and into the patient's lungs via the artificial airway. Exhaled air is carried through the first port 212a and then the second port 212b and out through the other ventilator tube. Thus, the manifold 204 forms part of a ventilation circuit 214 through which respiratory air is cycled. Also forming part of the manifold 204 is a third port 212c. The third port 212c is typically covered by a port cap 216.

Whenever mechanical ventilation is used, it is the goal to someday return the patient to voluntary or spontaneous breathing. To accomplish this, the patient must be weaned from the mechanical ventilation to spontaneous breathing, Accordingly, the port cap 216 may be removed from third port 212c, when present, so that oxygenated air may be provided to the patient's endotracheal tube, but this air is not forced into the patient's lungs by means of a closed circuit. This arrangement, commonly called blow-by, enables the patient to gradually resume natural or spontaneous breathing.

The manifold 204 may include a fourth port 212d. The fourth port 212d is disposed generally opposite the first port 212a and is configured to allow the catheter 208 to slide there through and into the first port 212a to enable suctioning of the patient. At the completion of suctioning, the catheter 208 is pulled back into the fourth port 212d to prevent interference with the ventilation circuit 214.

Disposed between the wall forming the fourth port 212d and the catheter 208 is a coupling or adaptor 220. On an outer extreme, the adaptor 220 engages the wall defining the fourth port 212d. On an inner extreme, the adaptor 220 engages a collar 224 that closely surrounds the catheter 208 so as to leave a small cylindrical space 226 around the catheter 208. Ideally, the space 226 between the catheter 208 and this collar 224 is between about 0.005 and about 0.015 inches. This proximity provides two advantages. First, if lavage needs to be provided to the lungs of the patient, injecting lavage solution through the lavage port 228 and into cylindrical space 226 causes stream of lavage solution to be directed out of the distal end 224a of the collar and through the first port 212a. If the spacing between the catheter 208 and the collar 224 is too large, the lavage solution cannot thus be directed. Second, as the catheter 208 is drawn back into the collar 224 after use, the collar helps to wipe any heavy layers of mucus or other secretions from the outside of the catheter.

Injecting lavage/cleaning solution through the lavage port 228 further removes the secretions from the exterior of the catheter 208 and enhances evacuation by suction in the catheter. This configuration also minimizes the volume of air and cleaning solution necessary to effect the cleaning.

A closeable flap 232 may be disposed inside the fourth port 212c As described and claimed, the term "flap" shall refer to any movable element formed of a resilient material capable of being opened or closed for the purposes described herein and which is distal to a lavage port and proximal to the ventilator port of the manifold. Flap 232 partitions it least one portion of at least one port 212a–212d of manifold 204 from the retracted catheter. Once flap 232 seals catheter 208, saline solution or similar cleaning lavages may be introduced via lavage port 228 to clean the assembly and/or the catheter 208. For this reason, it is important that flap 232 remain in tact and in working condition.

In operation, the catheter 208 pushes the flap into an open position. As depicted in FIG. 1A, flap 232 may be hingedly attached to an annular ring 236 disposed inside the fourth port 212d so as to enable the flap 232 to pivot with respect to the ring to form a self-closing valve member. This flap 232 could be attached directly to the wall of the manifold 204 defining the fourth port 212d or to the adapter 220. The hinged attachment 240 allows the flap 232 to selectively move from a closed position to an open position while maintaining alignment with the catheter tip, thereby creating a self-closing flap valve. The flap 232 is positioned to align with the distal end 208a of the catheter 208 when the catheter is almost completely withdrawn into the collar 224. The hinged attachment 240, like the flap, is of a sufficiently flexible material such that suction through the distal end 208a of the catheter 208 will draw the flap 232 proximally from open position into a closed position, wherein the flap may contact the distal end of the catheter. Thus, flap 232 and related structures form a self-closing valve wherein no additional extra manipulation of the catheter system is needed to close the valve.

Figure 1B:
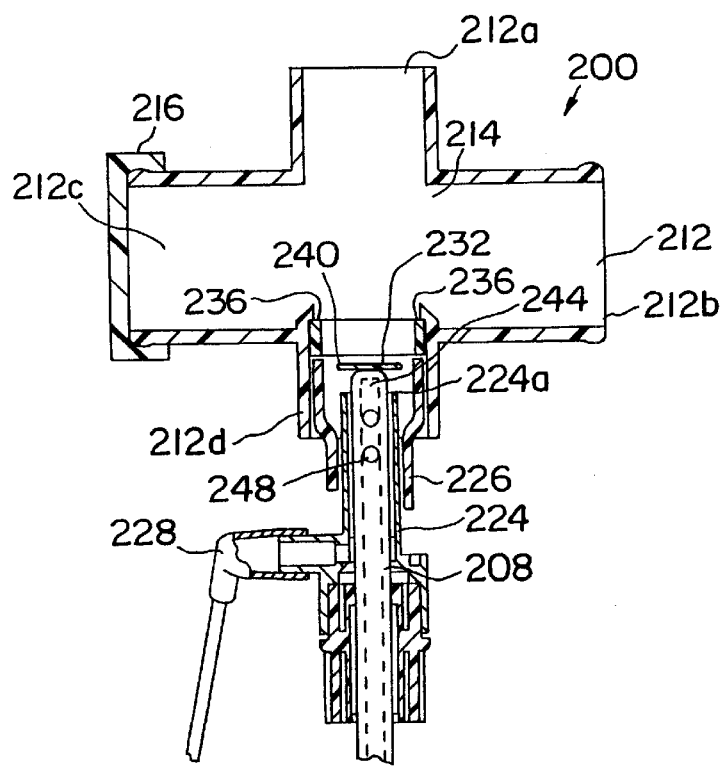
FIG. 1B shows a cross-sectional view of the representative manifold and catheter assembly shown in FIG. 1A, with the valve in a second, closed position.

Referring to FIG. 1B, when the flap 232 moves proximally and contacts the distal end 208a of the catheter 208, suction through catheter tip aperture 244, as is seen more clearly in FIG. 1C, is dramatically reduced or eliminated. This decrease in suction flow through the aperture 244 effectively increases the suction flow in the lateral apertures 248. Because the lateral apertures 248 are generally smaller than the distal aperture 244, as depicted in FIG. 1C, and because airflow to the lateral apertures 248 is limited by the collar 224, a substantial decrease in the amount of air withdrawn from the ventilation circuit 214 is achieved while simultaneously improving cleaning of the catheter 208. This redirection of suction flow will evacuate most secretions contained between the outside of the catheter 208 and the interior of the collar 224. Because of the very useful purpose that flap 232 performs in this situation, it is important that flap 232 is not damaged or otherwise deformed during shipping, storing, or other periods of nonuse.

Though flap 232 is generally planar, flap 232a, as shown in FIG. 1C, may have a channel 252 formed therein on the proximal side 232d. Moreover, flap 232d has an aperture 260 formed therein so as to allow a relatively small amount of air to pass through the flap 232b as shown in FIG. 1D. The diameter aperture 260 is sufficient to create a turbulent airflow at the distal end 208a of catheter 208. Due to the important purposes of flap 232, 232a, or 232b as disclosed herein, it is important for flap 232 to function properly and remain in working condition prior to use.

Figure 2A:
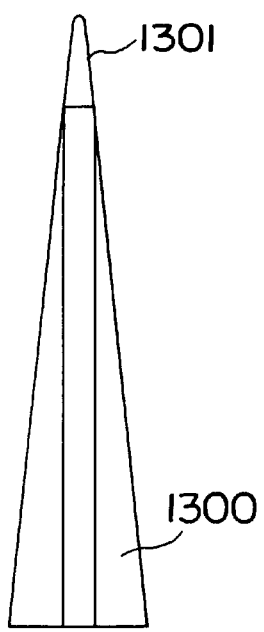
FIG. 2A shows a side view of a separator wedge in the prior art.
Figure 2B:
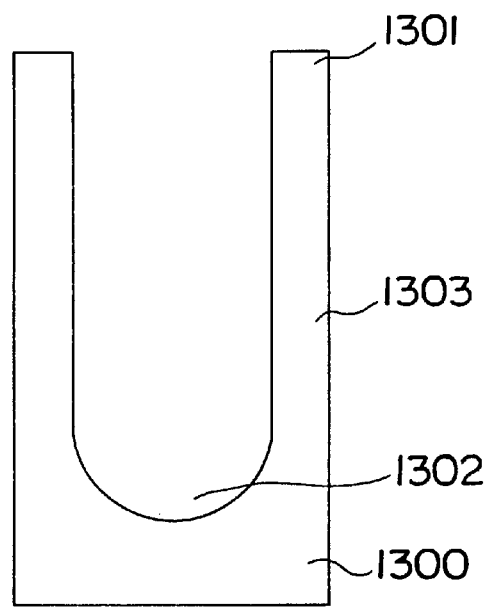
FIG. 2B shows a front view of the separator wedge in the prior art.
Figure 3A:
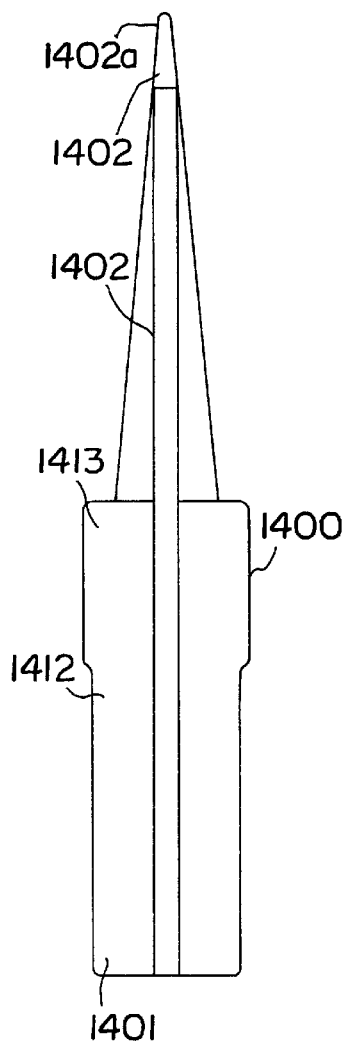
FIG. 3A shows a side view of an embodiment of the invention.
Figure 3B:
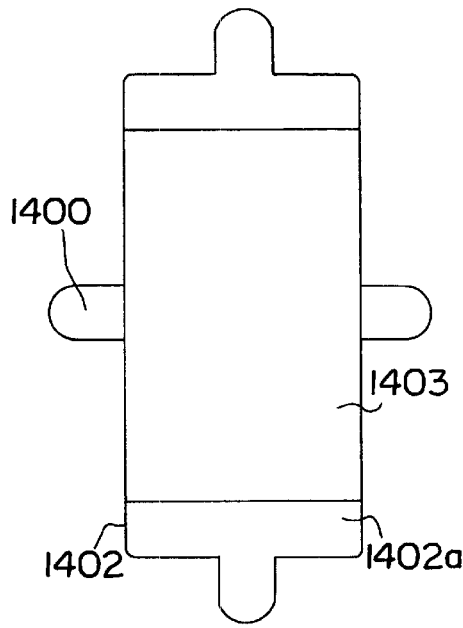
FIG. 3B shows a top view of the plug of FIG. 3A.
Figure 3C:
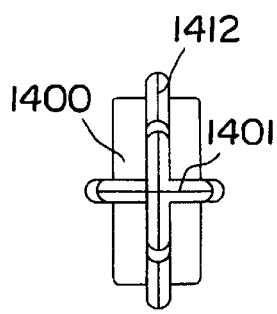
FIG. 3C shows a bottom view of the plug of FIG. 3A.
Figure 3D:
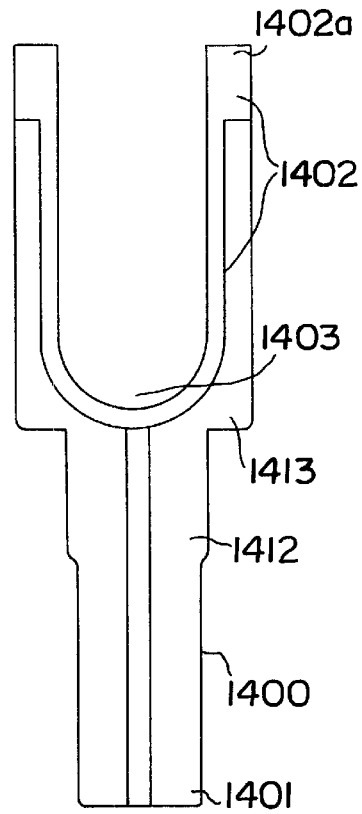
FIG. 3D shows a front view of the plug of FIG. 3A.
Figure 4A:
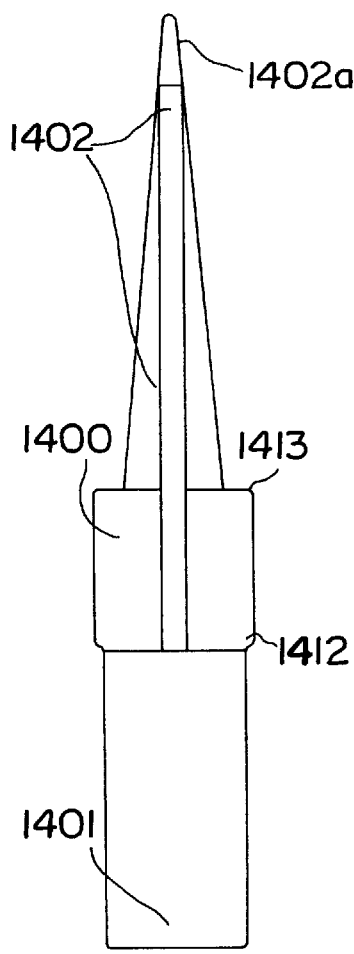
FIG. 4A shows a side view of another embodiment of the present invention.
Figure 4B:
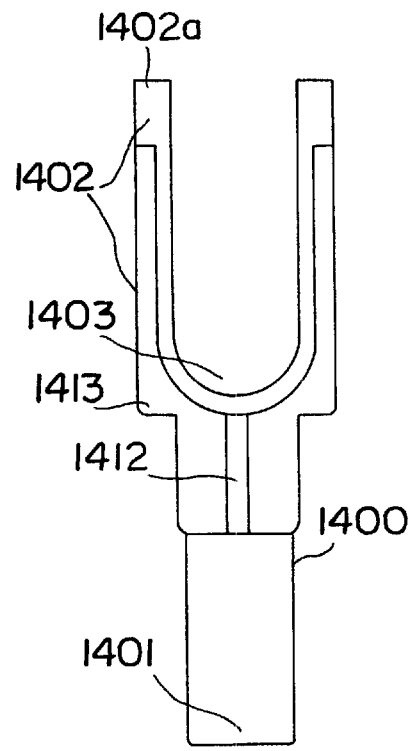
FIG. 4B shows a front view of the plug of FIG. 4A.
Figure 4C:
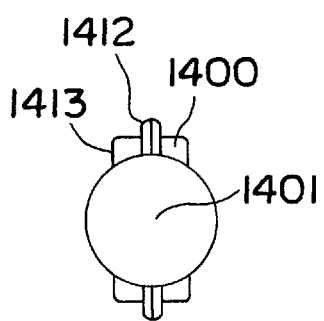
FIG. 4C shows a bottom view of the plug of FIG. 4A.
Figure 4D:
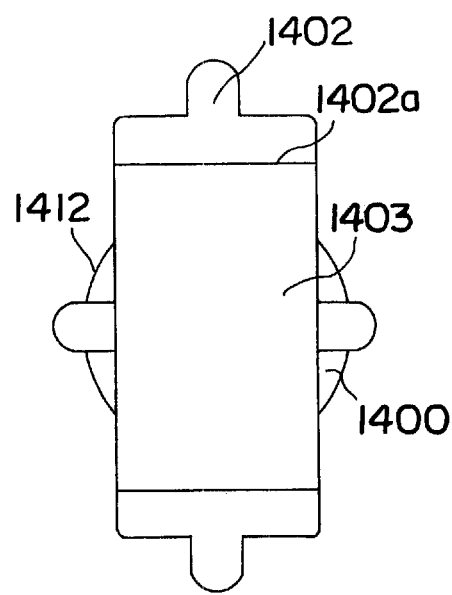
FIG. 4D shows a top view of the plug of FIG. 4A.

Though the prior art, as shown in FIGS. 2A and 2B, has included devices to aid in the separation of various components from the manifold, these devices have not offered any protection for the internal components of the catheter and manifold assembly. These devices have utilized U-shaped configurations to disengage components from the manifold 204 in very close proximity to the patient. As shown, wedge 1300 is characterized as having a wedge-like surface 1301 that is used to separate various components from the manifold. As shown in FIG. 2B, wedge 1300 is shown with a U-shaped configuration 1302 bordered by a plurality of tines 1303. These tines 1303 are formed such that the U-shaped configuration 1302 mall encircle at least a portion of the exterior surface of an attachment or adapter connected to the manifold itself. Due to the shape of the prior art device, however, wedge 1300 when used as a separation aid was in extremely close proximity to the contaminated exterior of the manifold. Such close proximity increased risk of contamination to the clinician as well as the patient. Finally, wedge 1300 bad to be separately packaged and sent with manifold and catheter assemblies.

Figure 6A:
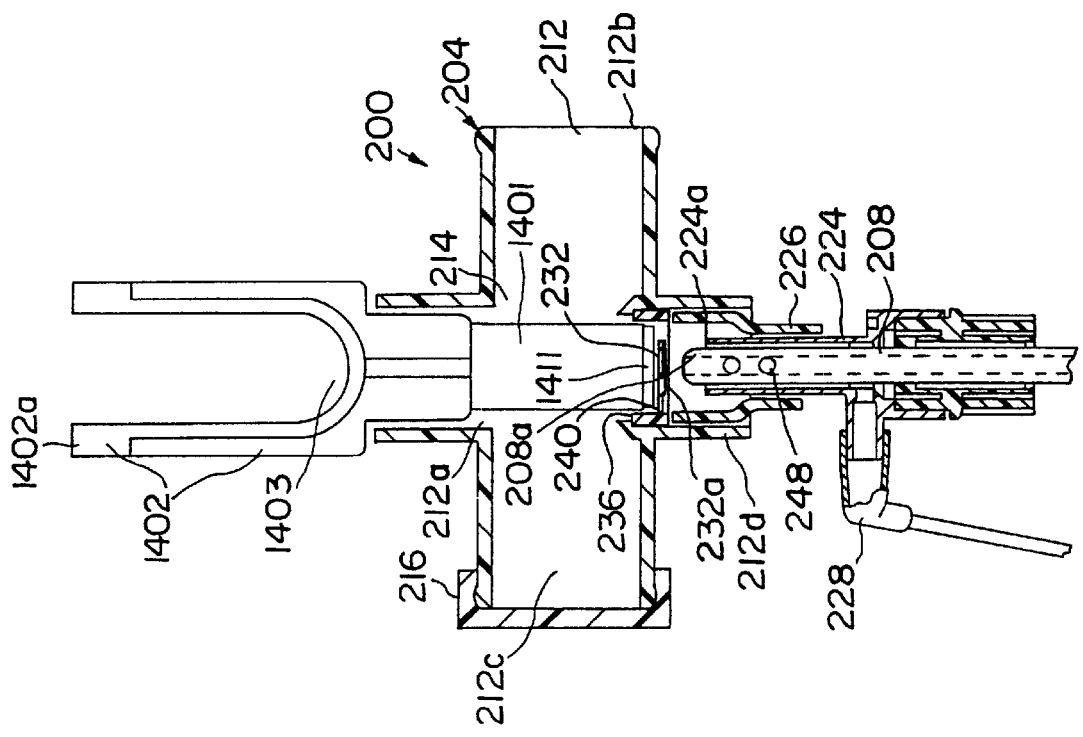
FIG. 6A shows an exploded front view showing the interior and exterior plug elements of the plug of FIGS. 4A–4D being inserted into a cross-sectional view of a representative manifold and catheter assembly.
Figure 6B:
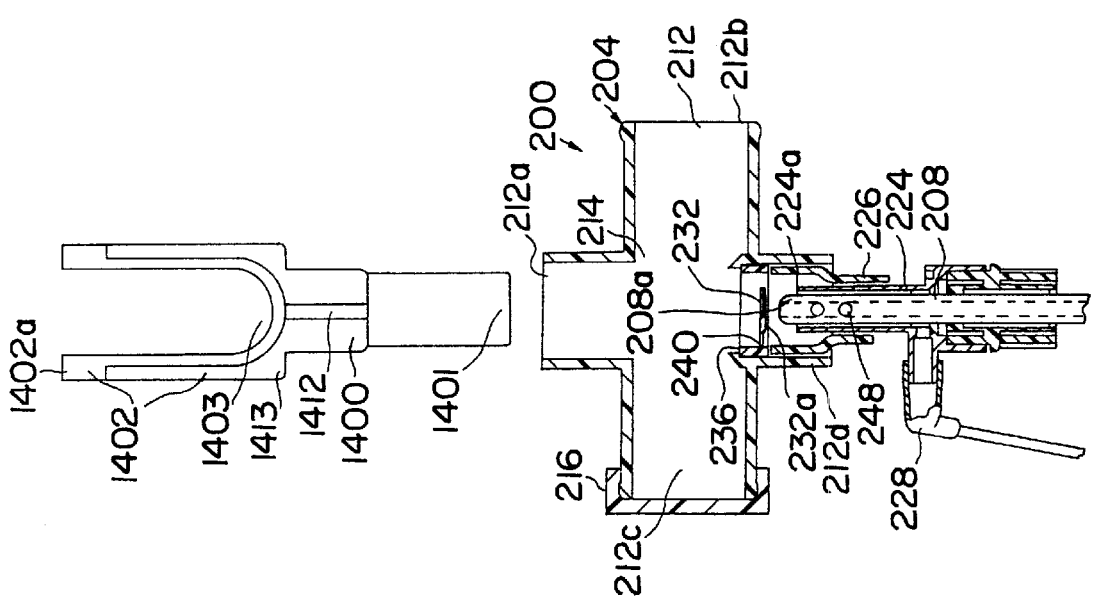
FIG. 6B shows a front view showing the interior and exterior plug elements of the plug of FIGS. 4A–4D inserted into a cross-sectional view of a representative manifold and catheter assembly.

Referring to FIGS. 3A–3D, an embodiment of the present invention, improves on the shortcomings of the prior art wedge. The retaining plug 1400 comprises an interior plug element 1401. In a preferred embodiment, the plug 1400 further has exterior plug element 1402. The dimensions of interior plug element 1401 are such that it can be inserted into the interior of manifold 204 within the internal passageway. The plug 1400 can then be inserted into port 212a, shown in FIG. 1A, such that interior plug element 1401 ultimately presses against flap 232 as shown in FIG. 6B. Moreover, plug 1400 may be formed with raised guides 1412 that aid in the proper insertion of plug 1400 into the manifold 204. Additionally, plug 1400 may be formed such that stops 1413 will prevent the exterior plug element 1402 from being inserted into the manifold 204. Stops 1413 prevent plug 1400 from damaging flap 232. In a preferred embodiment, the exteriormost portions of the interior plug element 1401 make frictional contact with the inner surface of port 212a once positive pressure is released. As a result, the position of plug 1400 is maintained within manifold 204.

Figure 8A:
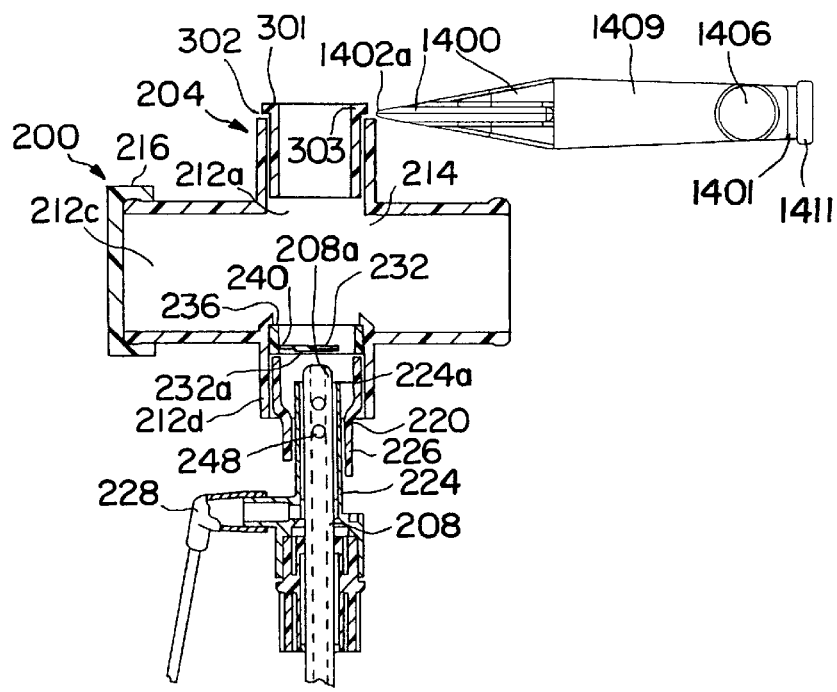
FIG. 8A shows an embodiment of the present invention comprising a wedge-like surface of the plug of FIGS. 5A–5D being used to separate at least two components of a cross-sectional view of a representative manifold and catheter assembly and attachments or adaptors thereto.
Figure 8B:
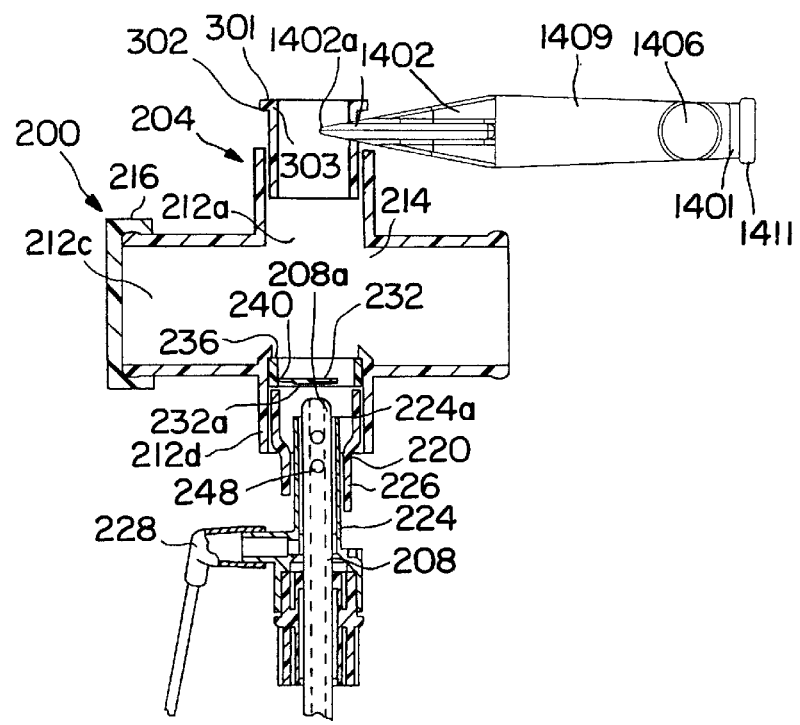
FIG. 8B shows an embodiment of the present invention comprising a wedge-like surface of the plug of FIGS. 5A–5D being used to separate at least two components of a cross-sectional view of a representative manifold and catheter assembly and attachments or adaptors thereto.

In another preferred embodiment, the exterior plug element 1402 comprises a wedge-like surface 1402a. As set forth in FIGS. 3B and 3D, the exterior plug element 1402 may consist of a U-shaped configuration 1403. The space created within this U-shaped configuration 1403 allows plug 1400 to be used to encompass at least a portion of the exterior of an attachment or adapter 301, as discussed in relation to FIGS. 8A–8F, connected to the manifold 204. The U-shaped configuration 1403 may be used to engage the outer exterior of an attachment or adapter 301 connected to the manifold and catheter assembly as shown in FIGS. 8B and 8C. Moreover, the U-shaped configuration 1403 of the exterior plug element 1402 requires only a minor amount of pressure or effort to separate attachment 301 from manifold 204 as shown by FIGS. 8A–8D.

Interior plug element 1401 fiber serves to increase the distance between the user and the possibly contaminated manifold and catheter assembly. In addition, the wedge-like surface 1402a may be used to separate releasably attached swivels 300, adapters 301, similar attachments to the manifold 204 with little or no discomfort to the patient FIGS. 8A–8D. It is preferable to use wedge-like surfaces 1402a on exterior plug element 1402 increase the grooves, channels, recesses, or fissure 302, as shown in FIGS. 8A–8D, to loosen or pry the attachment 301 from the manifold 204 or from the swivel 300 if included. As shown, the wedge like surface 1402a mill increase the fissure 302 such that attachment structure 301 separates from manifold 204 as is shown by FIGS. 8A–8C. Gentle twisting or turning of retaining plug 1400 may also assist in increasing fissure 302 when necessary.

It is envisioned that the interior plug element 1401 of plug 1400 will be inserted into the interior of manifold 204 prior to shipping manifold 204 to remote destinations or at other periods when the catheter tubing is inactive. At such times, the manifold 204 may be secured to the catheter sleeve. Because interior plug element 1401 of plug 1400, when inserted, holds flap 232 into a closed position, the chances of deformation of the shape of flap 232 or premature distal intrusion of catheter 208 are greatly reduced.

Moreover, the increased distance between the clinician and the components of assembly 200 offered by exterior plug element 1402 reduces the risk of contamination in those instances where plug 1400 is desired lo be used to separate the manifold 204 and releasable attachments at swivels 300, as shown in FIGS. 8B–8D, by using its wedge-like exterior end 1402a.

FIGS. 4A–4D show multiple views of another embodiment of the present invention. As shown, plug 1400 may be formed such that interior plug element 140, comprises a cylindrical, disk-like body which can be received within manifold 204. The use of a cylindrical configuration increases the exteriormost surface area that may engage the inner surface of the manifold 204. The result is the creation of more efficient friction causing the plug 1400 to remain secured once inserted. Further, the top portion of interior plug element 1401 can contain guide 1412 to guide the interior plug element 1401 into an abutting relationship with flap 232. Such guides may be comprised of raised ridges. As more clearly set forth in FIGS. 4C and 4D, interior plug element 1401 may comprise perpendicular guides 1412 that form a cross in a preferred embodiment. Additionally, the cylindrical configuration of interior plug element 1401 in this embodiment serves as a handle for the clinician separating components or attachments from the manifold 204, including separation of these assemblies from attachments when using the wedge-like surfaces 1402a that may be formed at exterior plug element 1402.

Figure 5A:
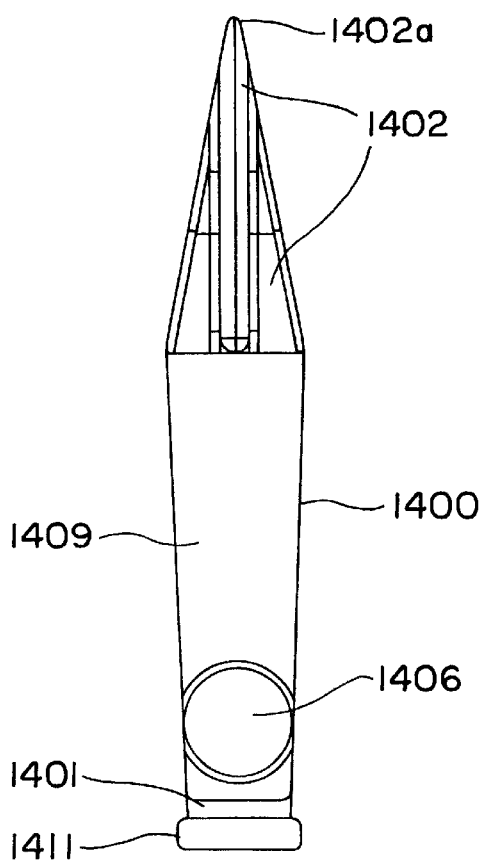
FIG. 5A shows a side view of a preferred embodiment of the present invention.
Figure 5B:
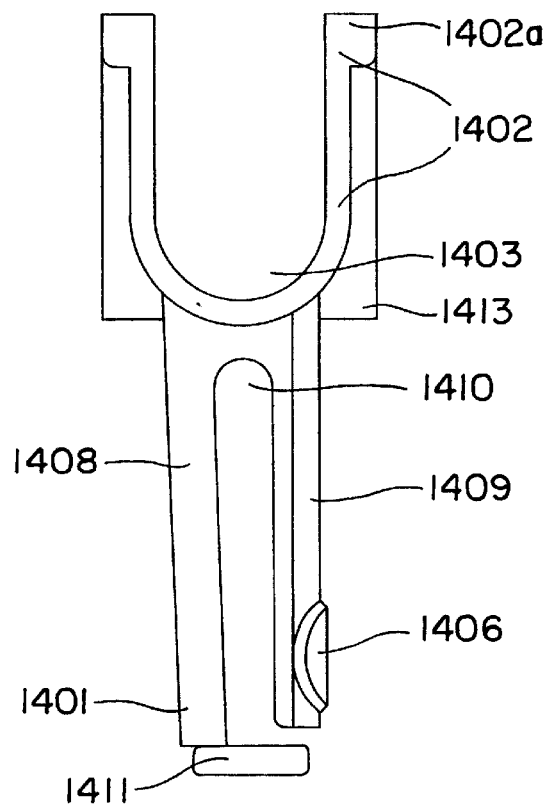
FIG. 5B shows a front view of the plug of FIG. 5A.
Figure 5C:
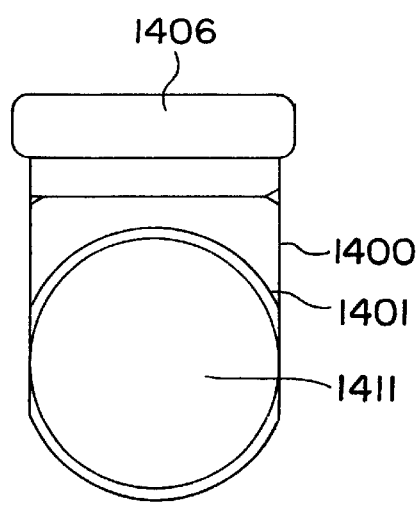
FIG. 5C shows a bottom view of the plug of FIG. 5A.
Figure 5D:
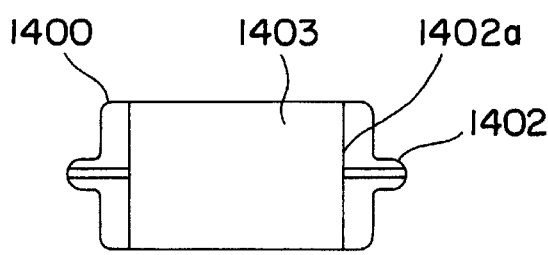
FIG. 5D shows a top view of the plug of FIG. 5A.
Figure 5E:
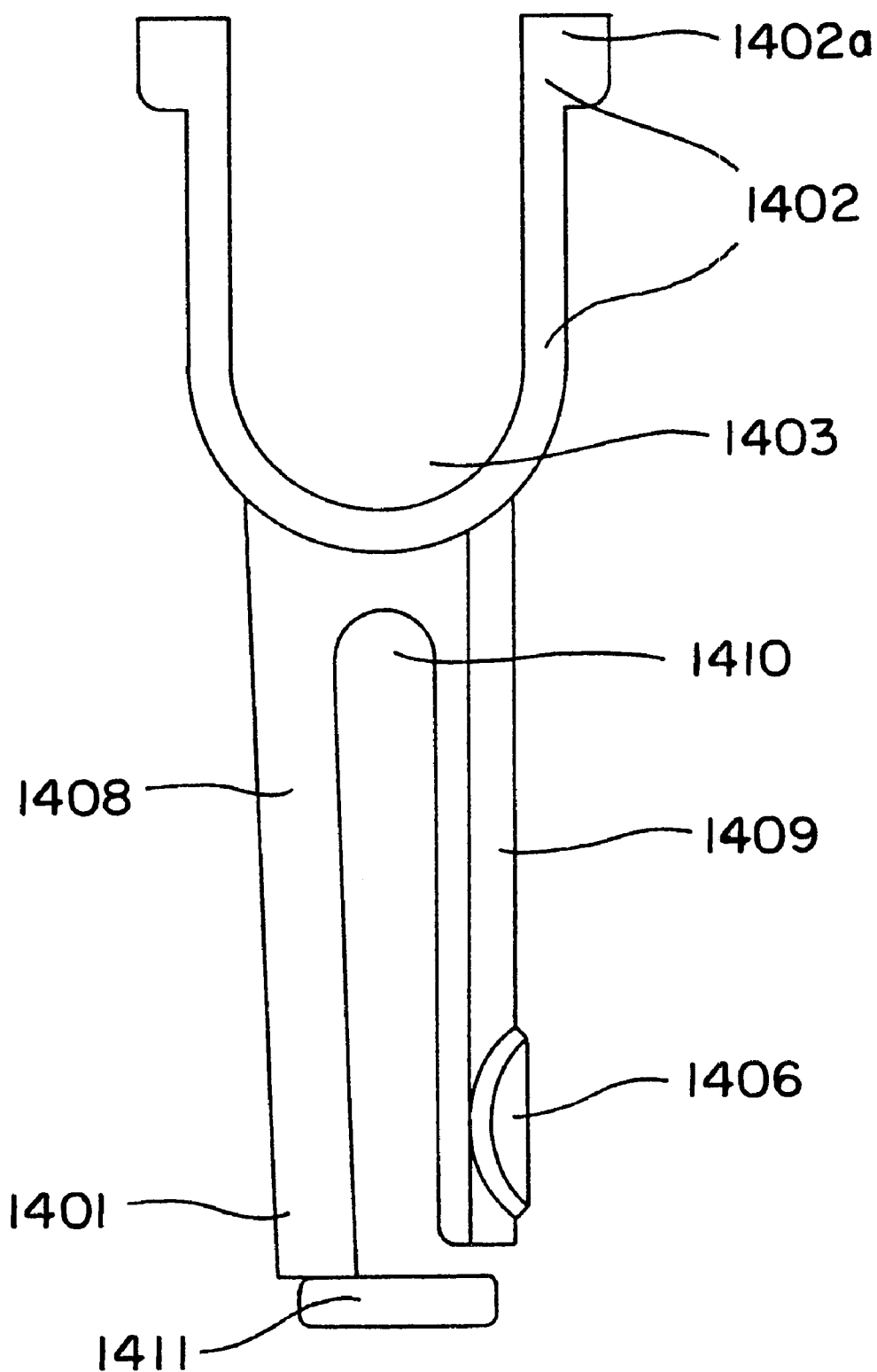
FIG. 5E shows a front view of an alternative embodiment of the present invention.
Figure 7B:
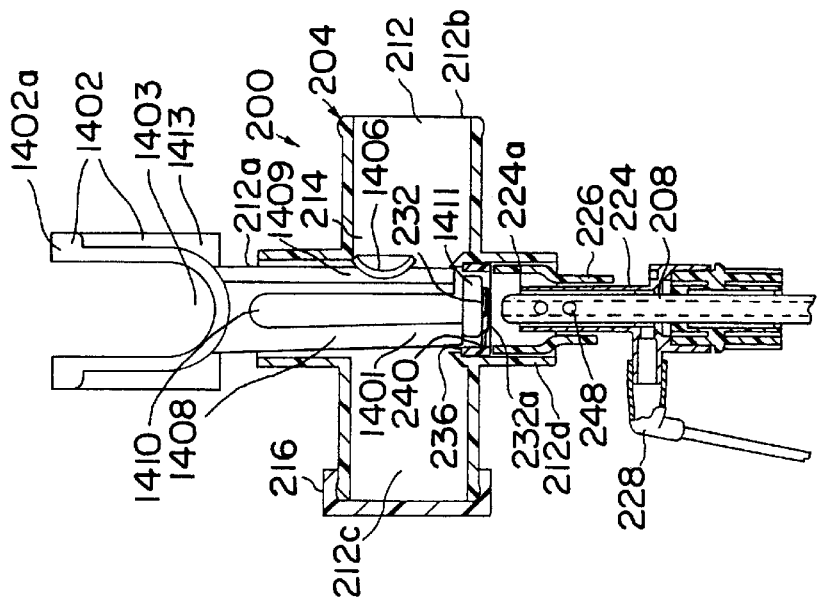
FIG. 7B shows a front view showing the interior and exterior plug elements of the plug of FIGS. 5A–5D inserted into a cross-sectional view of a representative manifold and catheter assembly.

FIGS. 5A–5D refer to a most preferred embodiment of the present invention, interior plug element 1401 may comprise a pair of radial arms 1408 and 1409 that define an inner cavity 1410. These radial arms 1408 and 1409 may be formed such that each engages flap 232 when plug 1400 is inserted. In a preferred embodiment, as shown in FIGS. 5A–5D, one arm of insertion end 1401 may be formed slightly longer, arm 1408 and FIG. 5B, such that an end cap 1411 may be formed or attached to the end of arm 1408. In this configuration, end cap 1411 will press flap 232 into the closed position when plug 1400 is inserted as shown in FIGS. 7B and 7D. Additionally, stops 1413, when formed into or attached to plug 1400, will prevent plug 400 from being inserted such that flap 232 is damaged. Though the preferred embodiment comprises formed stops 1413, these stop may be shaped such as shown in FIG. 5E. This embodiment reduces The amount of materials required to form the plug 1400.

Figure 7A:
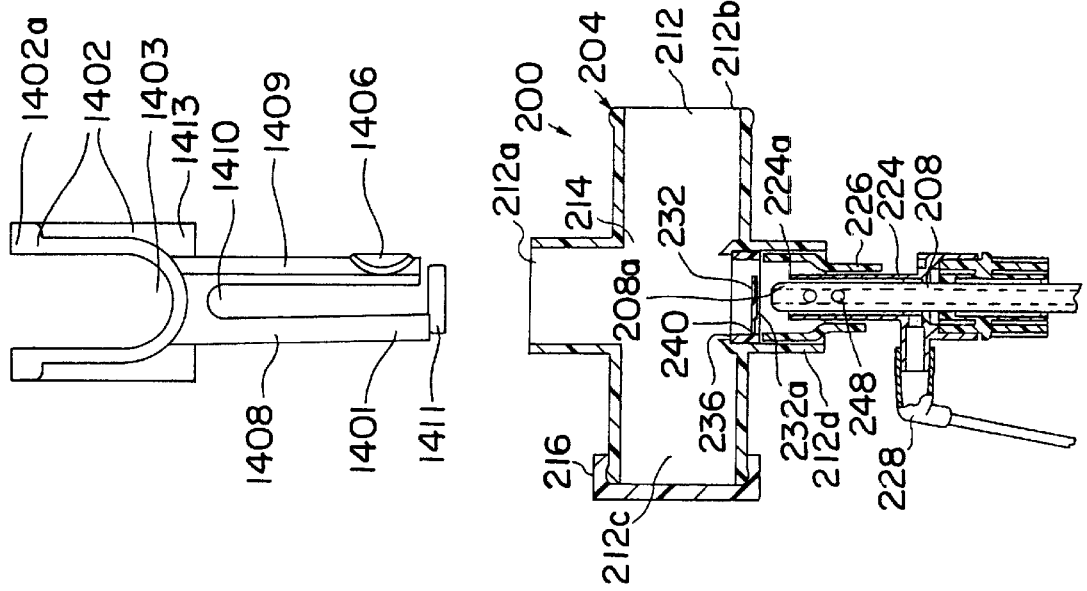
FIG. 7A shows a exploded front view showing the interior and exterior plug elements of the plug of FIGS. 5A–5D being inserted into a cross-sectional view of a representative manifold and catheter assembly.
Figure 7F:
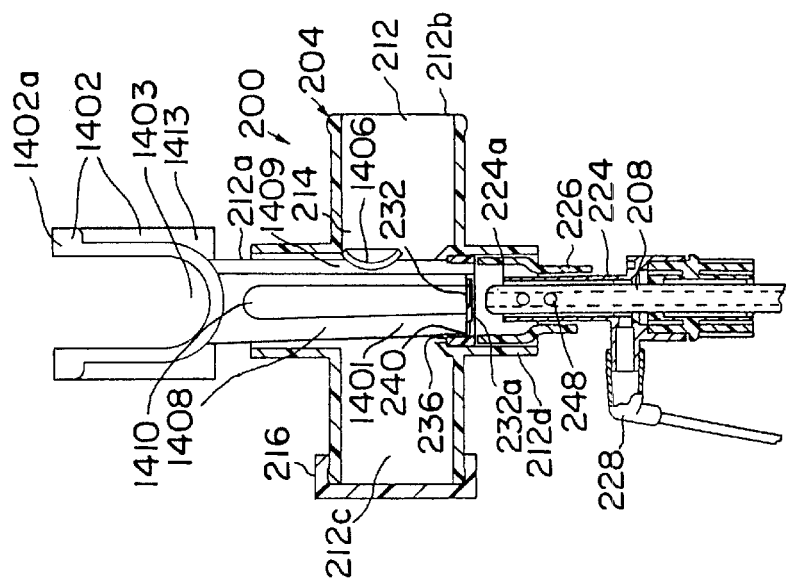
FIG. 7F shows a front view showing the interior and exterior plug elements of the plug of FIG. 7E inserted into a cross-sectional view of a representative manifold and catheter assembly.

Moreover, it is envisioned that at least one arm 1408 and/or 1409 may be formed such that it acts as a spring or similar expansion mechanism with position memory that may press against the interior surfaces of the catheter and manifold assembly 200 when plug 1400 is inserted as shown in FIG. 7F. Alternatively, this spring property is especially usefull when a preformed or attached knob 1406 is incorporated within or attached to at least one arm 1408 and/or 1409 such that knob 1406 is capable of engaging and expanding into at least one cavity, preferably port 212b of the manifold and catheter assembly 200. In this configuration, plug 1400 may be secured into position by the engagement of knob 1406 without any reliance on friction or pressure contacts with the other inner surfaces of the assembly 200 such as the arrangement depicted in FIGS. 7B and 7F. Many variations of spring property will be evident to those skilled in the art; it is envisioned that virtually any expansive mechanism may be used in this configuration.

Plug 1400 may be comprised of metal, plastic, rubber, or other resins that will not damage the interior of the manifold and catheter assembly. In a preferred embodiment plug 1400 is composed of a polycarbonate. Non-metallic materials are preferred in order to avoid the possibility of rusting.

Figure 7E:
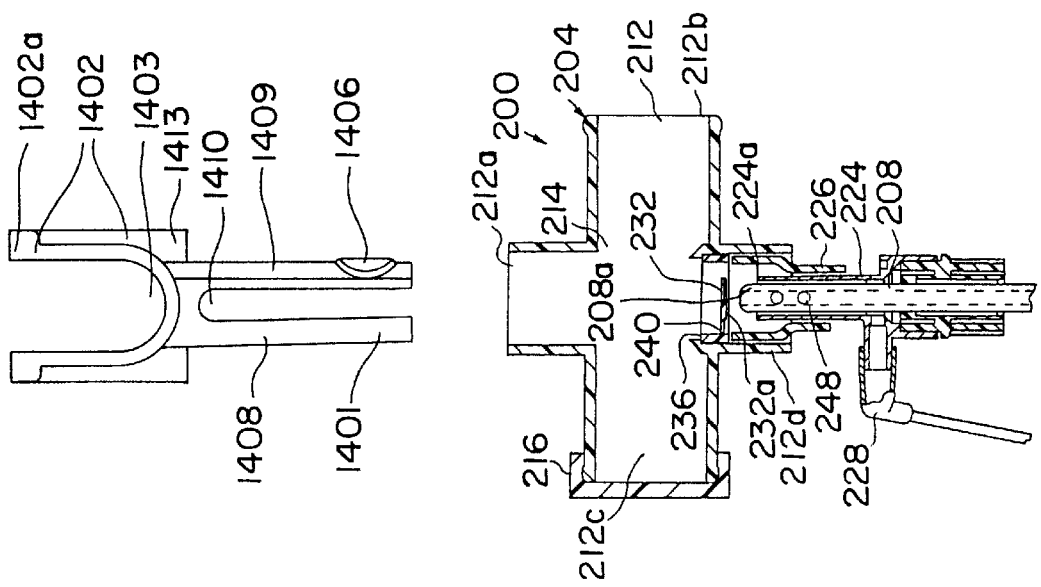
FIG. 7E shows an exploded front view showing the interior and exterior plug elements of an alternative embodiment of the present invention being inserted into a cross-sectional view of a representative manifold and catheter assembly.

As further shown in FIGS. 7A–7F, the interior plug element 1401 of plug 1400 preferably comprises two opposing arms 1408 and 1409 defining a cavity 1410 there between, including multiple novel and inventive aspects as disclosed herein. When inserted into catheter and manifold assembly, the spring property of arm 1409, when incorporated, expands such that the knob 1406, if included as shown in FIGS. 7A, 7B, 7E, and 7F, engages or otherwise occupies at least some portion of cavity 212b. In this relationship as shown in FIG. 7B, end cap 1411, if included, of the interior plug element 1401, or the ends of arms 1409 and 1408 when end cap 1411 is not formed or otherwise attached, as shown in FIGS. 7E and 7F, may snugly press flap 232 in a closed position such that catheter 208 will not prematurely distally extend during shipping or other periods of nonuse.

Of course, the plug embodiment set forth in FIGS. 7A–7B may include, as illustrated, exterior plug element 1402. As with the other embodiments of the present invention, these illustrations as shown in FIGS. 4A–4D and as shown in use in FIGS. 7A–7F may incorporate both the optional U-shaped configuration 1403 and the optional wedge-like surfaces 1402a at exterior plug element 1402 to enable the user of the invention the added benefits as discussed herein.

Referring to FIGS. 8A–8D and 8F, a representative catheter assembly is shown similar to the ones in FIGS. 1A–1D. Of note, the catheter and manifold assembly 200 further comprises at least one attachment structure 301. As shown in FIGS. 8A–8C, structure 301 is secured to port 212a. As shown in FIG. 8D this securing arrangement may include a swivel 300 that allows the interface between the structure 301 and manifold 204 that allows greater flexibility, freedom, and comfort for the patient. When included, swivel 300, as shown in close up FIG. 8F, allows attachment structure 301, interfacing at contact surface 304, to rotate and turn. This ability may compensate for the movements of the clinician and patient with respect to the assembly 200. By allowing a point of rotation in the assembly, the patient's comfort may be increased by reducing the possible pain associated with a twisted endotracheal tub attachment structure 301. Because these attachment structures 301 may be intimately connected with the patient, the amount of movement during these transitions can be very important. To this end, the swivel 300 allows for improved patient comfort by offering a greater amount of flexibility. Swivel 300 may be incorporated into any of the ports or any connection point with regard to the assembly 200.

Figure 8E:
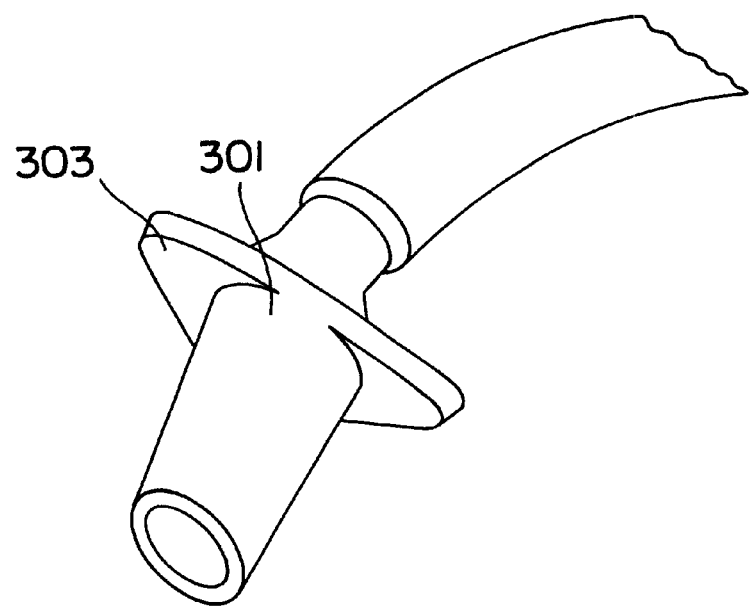
FIG. 8E shows a perspective view of a representative attachment in the form of an endotracheal tube.
Figure 8F:
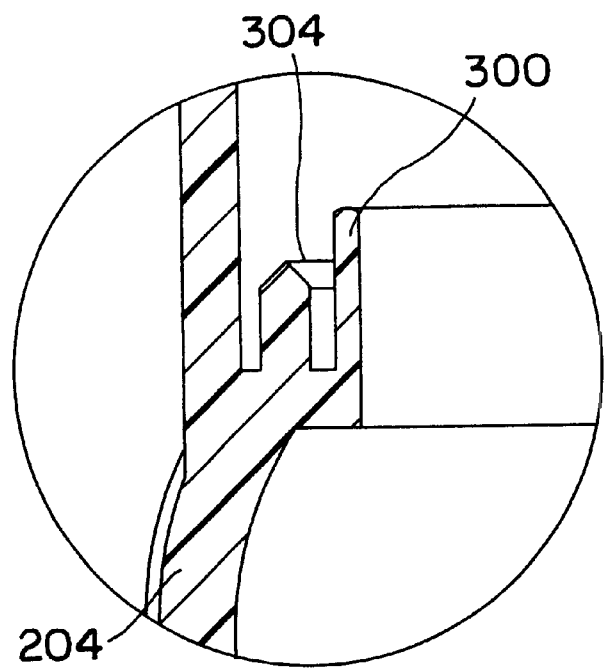
FIG. 8F shows a cross-sectional view close-up of the swivel connection of FIG 8D.

Due to the suctioning used within catheter and manifold assemblies, structures 301 become attached to the catheter and manifold assembly 200. As shown in FIG. 8A, a representative structure 301 is attached such that only a seam or fissure 302 exists between the manifold 204 and structure 301. Using an incorporated wedge-like surface 1402a on exterior end element 1402 the plug 1400 may be used to separate structure 301 from the catheter and manifold assembly 200. The insertion of wedge like surface 1402ainto fissure 302 should increase the fissure 302 as shown in FIG. 8B. The incorporation of the U-shaped configuration 1403 in the exterior plug element 1402 allows plug 1400 to advance and encompass at least part of the exterior surface of the attachment 301 as shown in FIG. 8C. As plug 1400 is gently advanced toward attachment 301, fissure 302 increases until attachment structure 301 may be separated from manifold 204. Because attachment structure may be an endotracheal tube such as shown in FIGS. 8D and 8E, it is important that plug 1400 may separate the attachment structure 301, the endotracheal tube in this embodiment, such that the patient's discomfort is not increased.

As shown in FIGS. 8A–8E, attachment structure 301 may comprise a flange 303 or similar lip to increase the ability of the wedge like surface 1402a of plug 1400 to gently pry into and ultimately increase fissure 302 until attachment structure 301 may be separated from the manifold 204. As previously discussed the extended length of plug 1400 allows the clinician to manipulate and separate these structures 301 from a greater distance than allowed with prior art devices. As a result, the risk of contamination may be reduced.

Figure 9B:
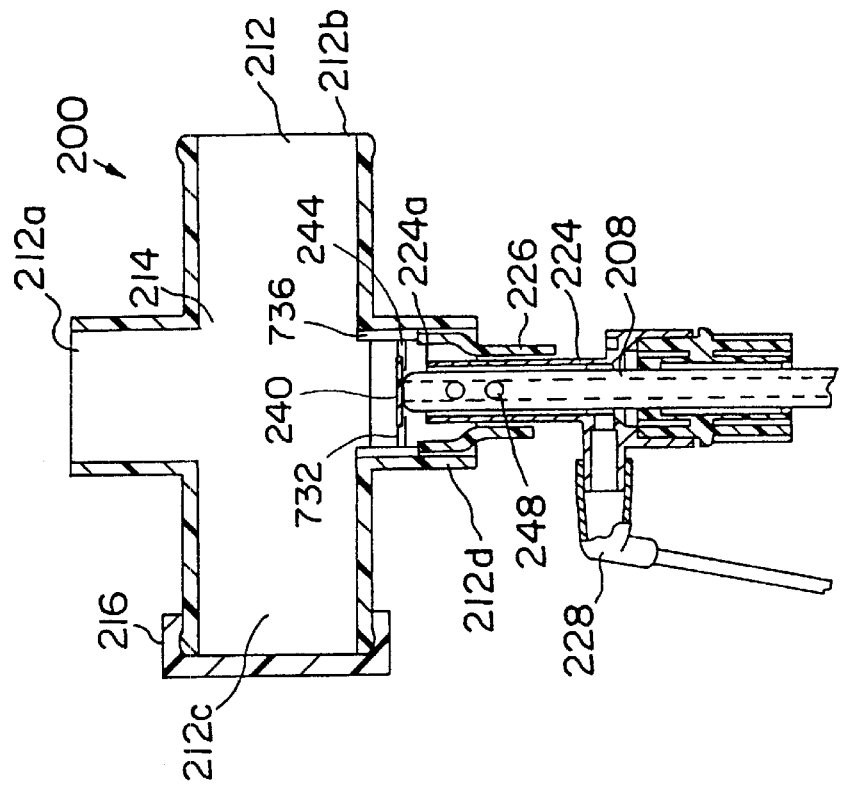
FIG. 9B shows a cross-sectional view of an improved endotracheal catheter wherein the flap is in a closed position.
Figure 9A:
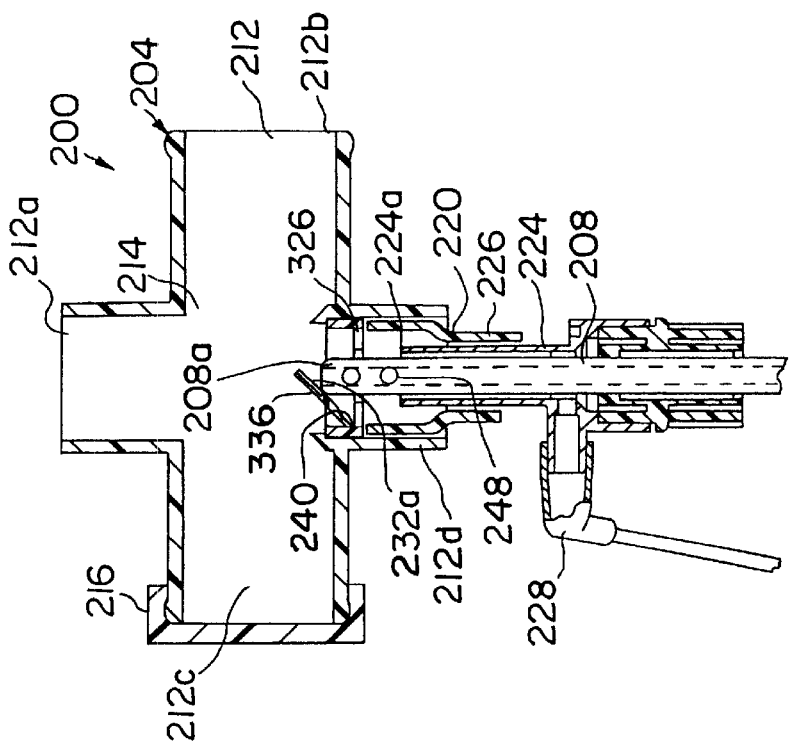
FIG. 9A shows a cross-sectional view of a alternative embodiment of an improved respiratory suction catheter apparatus having a valve in an open position.

Though plug 1400 has been shown in a representative catheter and manifold assembly 200, the present invention is design to protect the internal components of catheter and manifold assemblies that vary significantly from this representative catheter assembly. The present invention is envisioned to protect internal components of numerous variations and modifications of catheter and manifold assemblies. Referring to FIG. 9A, plug 1400 may be formed to engage flap 336 that is preferably hingedly attached to either the manifold directly or to annular ring 326. Though flap 732 in FIG. 9B engages the ring 736, plug 1400 may protect this configuration.

Figure 9C:
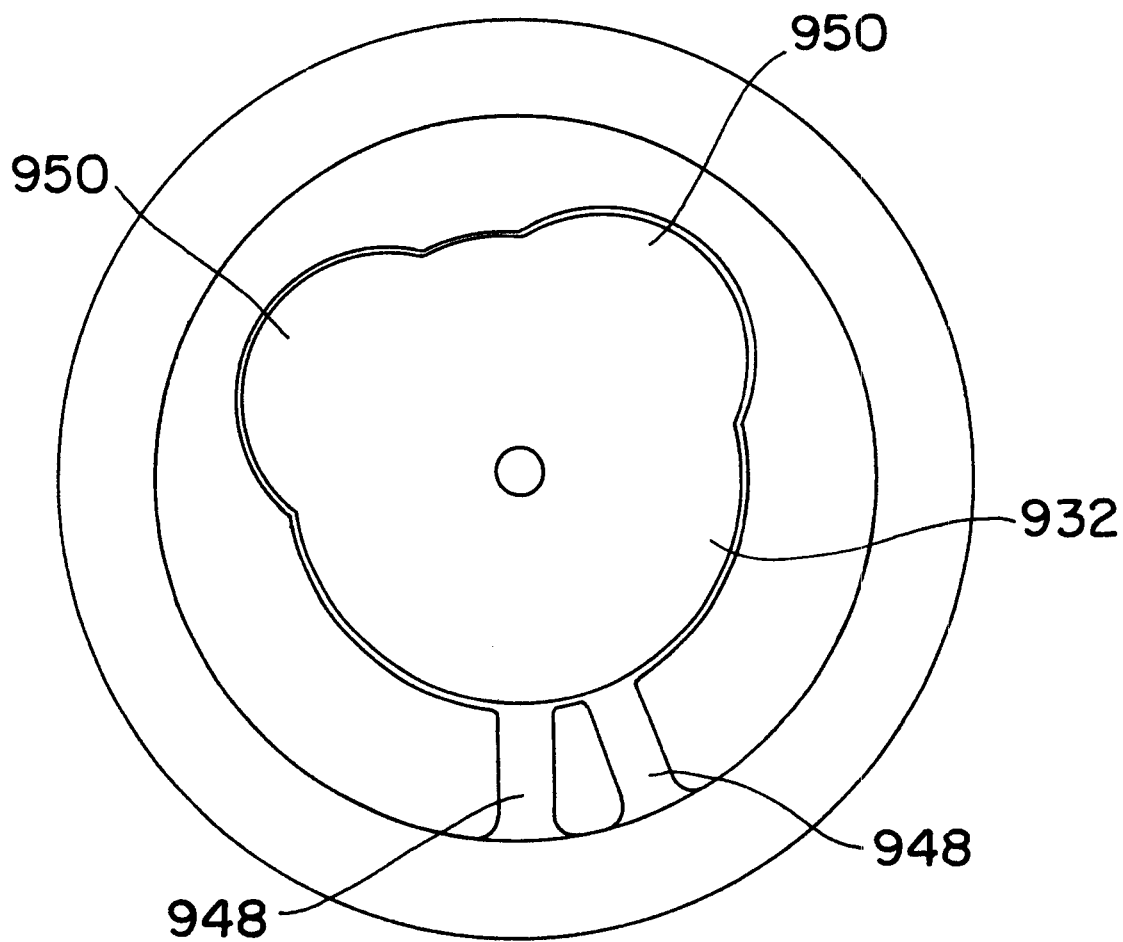
FIG. 9C shows a top view of an alternate embodiment of the flap shown in FIG. 5C.

When flap 932 is attached to the ring 936 by a pair of bridges 948, as shown in FIG. 9C, plug 1400 may still secure flap Though flap 932 has two rounded projections 950 which extend outwardly and are spaced approximately 90 degrees apart, plug 1400 may still press flap 932 into the closed position when properly inserted.

Those skilled in the art will appreciate modifications that can be made without departing from the scope and spirit of the present invention. The appended claims are intended to cover such modifications. Moreover, though reference was made to the drawings in which the various elements of the present invention were given numeral designations so as to enable one skilled in the art to make and use the invention, these designations should not narrow the following claims. Those skilled in the art will appreciate that aspects of the various embodiments discussed may be interchanged and modified without departing from the scope and spirit of the invention.

What is claimed is:

1. A respiratory suction catheter and retaining plug assembly comprising:
    a respiratory suction catheter assembly having an internal passageway extending through said respiratory suction catheter assembly and having a flap for opening and closing said internal passageway;
    a retaining plug configured to be inserted into said internal passageway and retained therein through frictional contact, said retaining plug configured to engage said flap and maintain said flap in a position to effect closure of said internal passageway;

wherein said retaining plug having an interior plug element and said interior plug element comprises two opposing arms between which is defined a cavity;

wherein at least one arm comprises a spring that expands against said internal passageway of said assembly when said retaining plug is inserted; and wherein said respiratory suction catheter assembly having at least one port, and wherein at least one arm having at least one knob capable of expanding into said at least one port when said retaining plug is inserted.

2. A plug for use in a respiratory suction catheter assembly, comprising:

an exterior plug element configured to be grasped by a user to withdraw or insert said plug; and an interior plug element connected to said exterior plug element, said interior plug element comprising:
 a pair of arms separate and spaced apart from and facing one another, said pair of arms defining a cavity therebetween;
 an end cap located on an outer most end of one of said arms of said pair of arms; and
 wherein at least one arm comprises at least one knob capable of expanding into at least one port of the respiratory suction catheter assembly when said plug is inserted into the respiratory suction catheter assembly.

3. A method of protecting a respiratory suction catheter assembly, comprising:

providing a respiratory suction catheter assembly having an internal passageway and having a flap for opening and closing said internal passageway;

inserting a retaining plug having an interior plug element into said internal passageway; and pressing said flap into a closed position by engaging said interior plug element and said flap, wherein said interior plug element comprises two opposing arms defining a cavity therebetween, wherein at least one arm comprises at least one knob that expands into at least one port of said respiratory suction catheter.

4. A respiratory suction catheter and retaining plug assembly, comprising:

a respiratory suction catheter assembly having an internal passageway extending through said respiratory suction catheter assembly and having a flap for opening and closing said internal passageway; and a retaining plug configured to be inserted into said internal passageway and retained therein through frictional contact, said retaining plug configured to engage said flap and maintain said flap in a position to effect closure of said internal passageway.

5. The assembly of claim 4, wherein said retaining plug having an interior plug element and said interior plug element is cylindrical.

6. The assembly of claim 4, wherein said retaining plug further comprises an exterior plug element that is U-shaped and contains two tines.

7. The assembly of claim 6, wherein a space formed between said two tines is capable of engulfing at least a portion of an exterior surface of an attachment or adapter connected to said assembly.

8. The assembly of claim 4, wherein said retaining plug having an interior plug element and said interior plug element comprises two opposing arms between which is defined a cavity.

9. The assembly of claim 8, wherein at least one arm comprises a spring that expands against said internal passageway of said assembly when said retaining plug is inserted.

10. The assembly of claim 8, wherein one of said arms of said interior plug element is longer than said other arm.

11. The assembly of claim 8, wherein the outermost end of at least one arm has an end cap capable of maintaining said flop in a position to effect closure of said internal passageway.

12. A plug for use in a respiratory suction catheter assembly, comprising:

an exterior plug element configured to be grasped by a user to withdraw or insert said plug; and an interior plug element connected to said exterior plug element, said interior plug element comprising:
 a pair of arms separate and spaced apart from and facing one another, said pair of arms defining a cavity therebetween; and
 an end cap located on an outermost end of one of said arms of said pair of arms.

13. The plug of claim 12, wherein said exterior plug element is U-shaped and comprises two tines.

14. The plug of claim 13, wherein the tines are configured to engage a structure attached to the respiratory suction catheter assembly and remove the structure from the respiratory suction catheter assembly.

15. The plug of claim 12, wherein at least one arm comprises a spring that expands against at least one inner surface of the respiratory suction catheter assembly when said plug is inserted into the respiratory suction catheter assembly.

16. A method of protecting a respiratory suction catheter assembly, comprising:

providing a respiratory suction catheter assembly having an internal passageway and having a flap for opening and closing said internal passageway;

inserting a retaining plug having an interior plug element into said internal passageway; and pressing said flap into a closed position by engaging said interior plug element and said flap.

17. The method of claim 16, wherein said interior plug element maintains said flap in a closed position due to friction between at least part of said interior plug element and at least a portion of the inner surfaces of said respiratory suction catheter assembly.

18. The method of claim 16, wherein said interior plug element comprises two opposing arms defining a cavity there between.

19. The method of claim 18, wherein at least one arm comprises a spring that expands into a port of said respiratory suction catheter assembly when inserting said retaining plug.

20. The method of claim 18, wherein at least one of the arms at the outermost end of said arm comprises an end cap that performs the step of pressing said flap into the closed position.

21. A plug for use in a respiratory suction catheter assembly, comprising:

an exterior plug element configured to be grasped by a user to withdraw or insert said plug from the respiratory suction catheter assembly; and an interior plug element connected to said exterior plug element, said interior plug element adapted to be inserted into an internal passageway of the respiratory suction catheter assembly, said interior plug element at least partially blocking the internal passageway of the respiratory suction catheter assembly when said plug is inserted into the respiratory suction catheter assembly.

22. The assembly of claim 21, wherein said interior plug element is cylindrical.

23. The assembly of claim 21, wherein at least a portion of said exterior plug element is U-shaped and contains two tines.

24. The assembly of claim 21, wherein said interior plug element comprises two opposing arms between which is defined a cavity.

25. The assembly of claim 24, wherein at least one arm comprises a spring that expands against the internal passageway when said plug is inserted.

26. The assembly of claim 24, wherein one of said arms of said interior plug element is longer than said other arm.

* * * * *